US011224378B2

(12) United States Patent
Anderson et al.

(10) Patent No.: US 11,224,378 B2
(45) Date of Patent: Jan. 18, 2022

(54) THERAPEUTIC LASER SYSTEM AND METHOD

(71) Applicants: Blossom Innovations, LLC, Waltham, MA (US); The General Hospital, Boston, MA (US)

(72) Inventors: Richard Rox Anderson, Boston, MA (US); Jayant Bhawalkar, Auburndale, MA (US); Dieter Manstein, Coral Gables, FL (US); Joseph Ting, Acton, MA (US); Vincent Zuo, Boston, MA (US); Lilit Garibyan, Brookline, MA (US); Kachiu Lee, Wynnewood, PA (US); Oge Onwudiwe, Silver Spring, MD (US); William A. Farinelli, Danvers, MA (US)

(73) Assignees: Blossom Innovations, LLC, Waltham, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 16/815,743

(22) Filed: Mar. 11, 2020

(65) Prior Publication Data
US 2020/0323483 A1 Oct. 15, 2020

Related U.S. Application Data

(60) Provisional application No. 62/818,987, filed on Mar. 15, 2019.

(51) Int. Cl.
*A61B 18/20* (2006.01)
*A61B 5/00* (2006.01)
(Continued)

(52) U.S. Cl.
CPC ............ *A61B 5/449* (2013.01); *A61B 5/0066* (2013.01); *A61B 5/0068* (2013.01);
(Continued)

(58) Field of Classification Search
CPC ....... A61B 18/18; A61B 18/20; A61B 18/201; A61B 18/203; A61B 2018/00315;
(Continued)

(56) References Cited

U.S. PATENT DOCUMENTS 6,050,990 A * 4/2000 Tankovich ........... A61B 18/203
606/16
8,523,926 B2 * 9/2013 Neev ...................... C12N 13/00
(Continued)

FOREIGN PATENT DOCUMENTS

WO 2020/190376 A1 9/2020

OTHER PUBLICATIONS

International Search Report and Written Opinion for corresponding International Application No. PCT/US20/22255, dated Jun. 12, 2020, 13 pages.

*Primary Examiner* — Ahmed M Farah
(74) *Attorney, Agent, or Firm* — Mintz Levin Cohn Ferris Glovsky and Popeo, P.C.

(57) ABSTRACT

A treatment system can include a channel generation system configured to expose an infected region of a target tissue with a laser beam traveling along an optical axis and focused at a focal volume located in or adjacent to the target tissue. The laser beam can have a wavelength ranging from about 100 nm to about 400 nm. The laser beam can be configured to generate at least a first channel in the infected region. The treatment system can also include a detection system configured to detect a first radiation generated by one or more of (i) the target tissue, (ii) a fungi coupled to the infected region in the target tissue, and (iii) an adjacent tissue located proximal to the target tissue as a result of interaction with the laser beam. The treatment system can also include a delivery system configured to deposit an active treatment agent in the at least first channel.

31 Claims, 20 Drawing Sheets

(51) Int. Cl.
*A61B 17/54* (2006.01)
*A61M 37/00* (2006.01)
*A61K 45/06* (2006.01)
*A61M 11/00* (2006.01)
*A61M 3/00* (2006.01)

(52) U.S. Cl.
CPC .......... *A61B 5/0071* (2013.01); *A61B 5/4839* (2013.01); *A61B 17/54* (2013.01); *A61K 45/06* (2013.01); *A61M 37/0092* (2013.01); *A61M 3/00* (2013.01); *A61M 11/00* (2013.01); *A61M 2037/0007* (2013.01); *A61M 2205/36* (2013.01)

(58) Field of Classification Search
CPC .. A61B 2018/00452; A61B 2018/0047; A61B 2018/00636; A61B 5/44; A61B 5/441; A61B 5/444; A61B 5/445; A61B 5/448; A61B 5/449; A61B 5/4839; A61B 5/0059; A61B 5/0066; A61B 5/0071; A61N 5/06; A61N 5/0613; A61N 5/0616; A61N 5/062; A61N 5/0624; A61N 2005/0626; A61M 37/00; A61M 2037/0007; A61M 2037/0015; A61M 2037/0023; A61M 2037/0069; A61M 2037/0092; A61M 11/00; A61M 11/001; A61M 11/005; A61M 11/006; A61M 11/007; A61M 3/00; A61M 3/02; A61M 3/00233; A61L 35/44; A61L 35/441; A61L 35/444; A61L 35/448; A61L 35/449; A61L 35/4839
USPC ................................ 606/3, 9–17; 607/88, 89
See application file for complete search history.

(56) References Cited

U.S. PATENT DOCUMENTS

| | | |
|---|---|---|
| 2003/0105163 A1 | 6/2003 | Kennedy et al. |
| 2003/0181847 A1* | 9/2003 | Bruno-Raimondi ... A61K 41/00 604/20 |
| 2009/0069741 A1 | 3/2009 | Altshuler et al. |
| 2010/0191215 A1 | 7/2010 | Globerman et al. |
| 2011/0015549 A1* | 1/2011 | Eckhouse .............. A61B 18/14 601/3 |
| 2013/0023966 A1 | 1/2013 | Depfenhart et al. |
| 2013/0211481 A1* | 8/2013 | Ward ................... A61N 5/0624 607/89 |
| 2014/0277295 A1 | 9/2014 | Yoo |
| 2014/0316387 A1* | 10/2014 | Harris .................. A61K 8/0283 606/3 |
| 2020/0289844 A1 | 9/2020 | Anderson et al. |

* cited by examiner

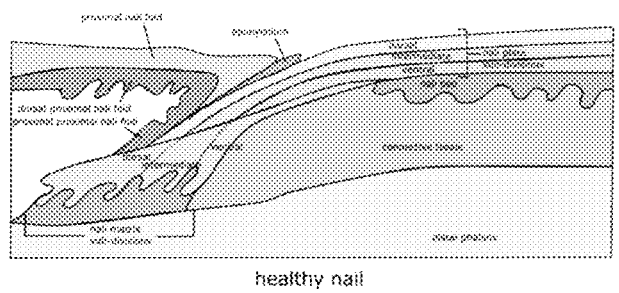
FIG. 2A
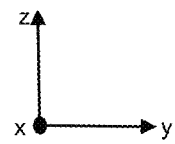
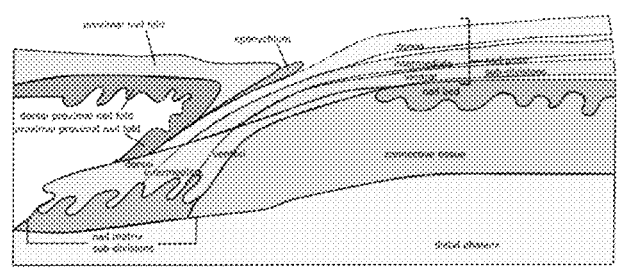
FIG. 2B
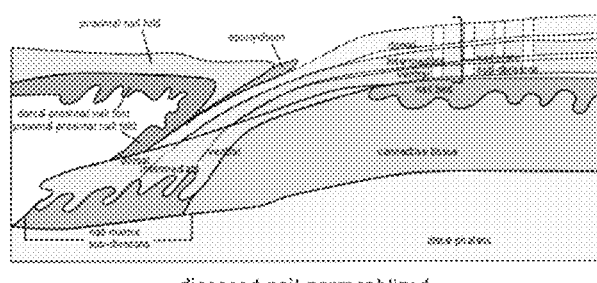
FIG. 2C

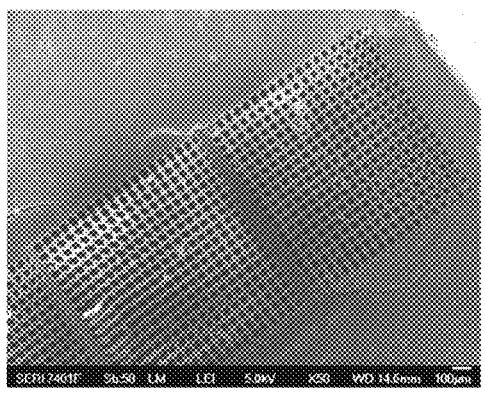 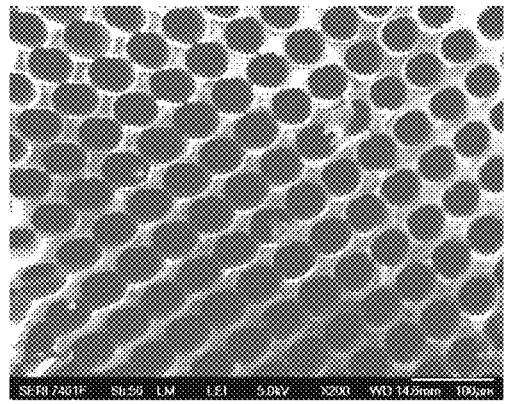
FIG. 5A                    FIG. 5B

Fig. 6. Calcein images, pore permeability index, and histogram of fluorescent intensity of laser-treated bovine hoof membrane (A, F, K) 3P-2D, (B, G, L) 3P-1.5D, (C, H, M) 3P-1D, (D, I, N) 2P-2D, (E, J, O) 4P-2D.

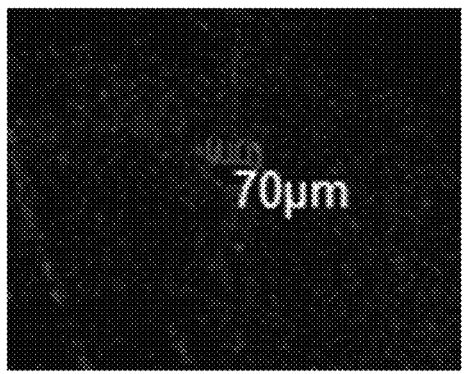 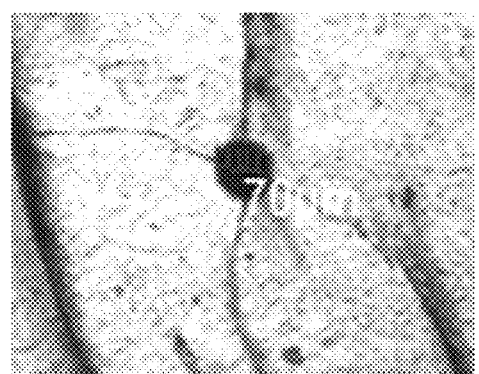
FIG. 12A                    FIG. 12B

THERAPEUTIC LASER SYSTEM AND METHOD

RELATED APPLICATION

This application claims priority under 35 U.S.C. § 119(e) to U.S. Provisional Patent Application No. 62/818,987 filed on Mar. 15, 2019, the entire contents of which are hereby expressly incorporated by reference herein.

BACKGROUND

Onychomycosis is a fungal infection of the nails that can cause discoloration, thickening, and separation of nail from the nail bed. Affected nails tend to be cosmetically unattractive. It accounts for about 50% of nail disorders. Approximately 2-8% of the worldwide population are affected by onychomycosis. It can be caused by a variety of organisms (e.g., dermatophytes, yeasts, non-dermatophyte molds, etc.). The majority of fungal nail infection are caused by dermatophytes, and toenails are generally more affected than fingernails. The dermatophytes can exist in an active form, hyphae (filamentous cells) and a passive form, spores from which hyphae reproduce. Both forms can become deeply embedded in the nail plate. Fungal infection can be complicated in those suffering from other medical conditions (e.g., diabetes, peripheral vascular diseases, immune diseases, etc.). Onychomycosis treatment can be classified based on the location of infection (e.g., toes, fingers, etc.).

Accurate diagnosis of onychomycosis can involve physical and microscopic examination and culture. Histologic evaluation using periodic acid-Schiff staining can increase sensitivity for detecting infection. Treatment of onychomycosis can lead to eradication of the causative organism (e.g., dermatophytes, yeasts, non-dermatophyte molds, etc.) that can return an infected nail to its normal appearance. The systemic administration of anti-fungal drugs are a viable treatment but have limited efficacy, are hepatotoxic, pose other serious side effects, and interact strongly with common statin drugs. The application of topical solutions of anti-fungal drugs can provide limited relief to the infected nail because 1) the solutions can be effective against dermatophytes in hyphae form and not very effective against spores which can later create more hyphae, and 2) it can be difficult for the solutions to penetrate the nail plate. Laser-based therapies have shown some potential for providing treatment of onychomycosis, but methods employed thus far have had limited efficacy, are approved for temporary clearance only, and do not provide a cure.

Existing methods for treating onychomycosis can also include application of topical ointments (e.g., anti-fungal drugs) on the surface of the nail affected by onychomycosis. However, such treatment methods can have limited efficacy. For example, the topical ointment may have limited penetration through the nail plate (e.g., due to layered structure of the nail plate described above). Moreover, the topical ointment may not remain on the nail plate long enough to diffuse through the various layers of the nail plate (e.g., contact between the nail plate and an external object (e.g., socks, shoes, etc.) can remove the topical ointment. Alternately, treatment methods can involve surgery (e.g., nail avulsion) that can be painful, can lead to infection, and can require a long healing period.

SUMMARY

Accordingly, improved methods, systems, and devices for treatment of fungal infection (e.g., onychomycosis) are provided.

A treatment system can include a channel generation system configured to expose an infected region of a target tissue with a laser beam traveling along an optical axis and focused at a focal volume located in or adjacent to the target tissue. The laser beam can have a wavelength ranging from about 100 nm to about 400 nm. The laser beam can be configured to generate at least a first channel in the infected region. The treatment system can also include a detection system configured to detect a first radiation generated by one or more of (i) the target tissue, (ii) a fungi coupled to the infected region in the target tissue, and (iii) an adjacent tissue located proximal to the target tissue as a result of interaction with the laser beam. The treatment system can also include a delivery system configured to deposit an active treatment agent in the at least first channel.

In one implementation, the treatment system can further include a controller configured to receive a first detection signal from the detection system indicative of the detected first radiation, and determine the identity of the fungi coupled to the infected region in the target tissue. In another implementation, the first radiation is at least one of a fluorescence from the fungi and a fluorophore coupled to the fungi. In one implementation, the fluorophore includes one or more of 5-ALA, an ester of ALA, and ppIX.

In one implementation, the channel generation system is configured to generate at least a second channel adjacent to the first channel. The at least second channel is configured to receive the active treatment agent. The received active treatment agent in the first and second channels is configured to diffuse to portions of the target tissue adjacent to the first channel and the second channel. In another implementation, the target tissue is a nail plate and the adjacent tissue is a nail bed tissue, and the first channel extends from a top proximal surface of the nail plate and a bottom distal surface of the nail plate, the bottom distal surface of the nail plate adjacent to a nail bed tissue. The detection system is configured to detect a second radiation generated due to interaction between the laser beam and the nail bed tissue, and transmit a second detection signal indicative of interaction between the laser beam and the nail bed tissue. The channel generation system is configured to terminate interaction between the laser beam and the nail plate based on reception of second detection signal.

In one implementation, the treatment system can further include a drilling system configured to generate one or more drilled holes in the target tissue. In another implementation, the treatment system can further include a driving system configured to drive the active treatment agent in the first channel by one or more of application of modulated pressure waves to the target tissue, application of heat to the target tissue, and application of an ultrasound wave to the target tissue. The modulated pressure wave can be generated by directing a second laser beam on the target tissue. In one implementation, the delivery system is configured to deposit the active treatment agent in the first channel by at least spraying the active treatment agent into the first channel.

In one implementation, the delivery system includes a syringe comprising a disposable unit package comprising the active treatment agent and a sealant tip configured to be applied to the first channel after the deposition of the active treatment agent. In another implementation, the active treatment agent includes one or more of a particulate, a liposome, a gel, a polymer, an emulsion, an ointment, and a suspension. A cross-section of the first channel can be oriented perpendicular to the optical axis can be one of circle, oval or rectangle. In one implementation, the channel generation system is configured to generate an array of channels in the target tissue based on one or more of a square pattern, a triangular pattern, and a quasi-random pattern. A pitch of the array of channels is based on a degree of infection in the target tissue.

In one implementation, the array of channels are generated by a plurality of laser sub-beams generated by splitting the laser beam into the plurality of sub-beams. In another implementation, a distance between the centers of adjacent channels in the array of channels is one of between 2 and 10 times, between 3 and 7 times, between 4 and 6 times, and between 4 and 5 times the diameter of a channel in the array of channel. A diameter of the channel at a proximal opening of the channel can be in the range of about 30 microns to 200 microns. A spot diameter associated with the focal volume can be about 1 to about 25 micrometers. The active treatment agent can include one or more of an anti-fungal drug approved for the treatment of onychomycosis.

A treatment method can include exposing an infected region of a target tissue to a laser beam having a wavelength in the range of about 100 nm to about 400 nm and traveling along an optical axis and focused at a focal volume located in or adjacent to the target tissue to form a plurality of separate channels in a predetermined pattern. Each of the channels extend from a top proximal surface of the target tissue to a bottom distal surface of the target tissue proximal to an adjacent tissue and each of the channels have an opening at the top proximal surface thereof with a dimension in the range of about 30 to 200 microns. The method can further include detecting a first radiation generated by one or more of the target tissue, a fungi coupled to the infected region in the target tissue, and the adjacent tissue located proximal to the target tissue as a result of interaction with the laser beam. The method can further include depositing an active treatment agent in at least one of the channels.

In one implementation, the target tissue is a nail plate and the adjacent tissue is a nail bed tissue. In another implementation, the method can further include receiving, via a controller, a first detection signal indicative of the detected first radiation, and determining the identity of the fungi coupled to the infected region in the target tissue. In one implementation, the method can further include detecting a second radiation generated due to interaction between the laser beam and the nail bed tissue; transmitting a second detection signal indicative of interaction between the laser beam and the nail bed tissue; and terminating the interaction between the laser beam and the nail plate based on reception of second detection signal.

In one implementation, the method can further include determining, via the controller, a depth associated with the first channel using at least one of reflectance confocal microscopy and optical coherence tomography. In another implementation, the method can further include driving the active treatment agent in at least one of the channels by one or more of applying modulated pressure waves to the target tissue, applying heat to the target tissue, and applying an ultrasound wave to the target tissue. In one implementation, the method can further include applying a sealant tip to the channels after the deposition of the active treatment agent. The active treatment agent is applied via delivery system that includes a syringe comprising a disposable unit package comprising the active treatment agent and the sealant tip. In one implementation, the method can further include softening the target tissue prior to exposure to the laser beam. The active treatment agent is at least one anti-fungal drug approved for the treatment of onychomycosis.

BRIEF DESCRIPTION OF THE DRAWINGS

Embodiments of the disclosure will be more fully understood from the following detailed description taken in conjunction with the accompanying drawings, in which:

FIG. 2A illustrates a cross-section of the nail apparatus in FIG. 1;

FIG. 2B illustrates the effects of onychomycosis on the structure of a nail;

FIG. 2C illustrates the effect of permeabilizing a diseased nail to provide direct access to the nail bed;

FIG. 5A illustrates a scanning electronic microscopic (SEM) image of an exemplary array of channels in a nail plate;

FIG. 5B illustrates a magnified version of the image in FIG. 5A;

FIGS. 12A and 12B are micrographs illustrating exemplary effect of vacuum/pressure on delivery of the dye solution through micro-channels generated using excimer laser;

Figure 1:
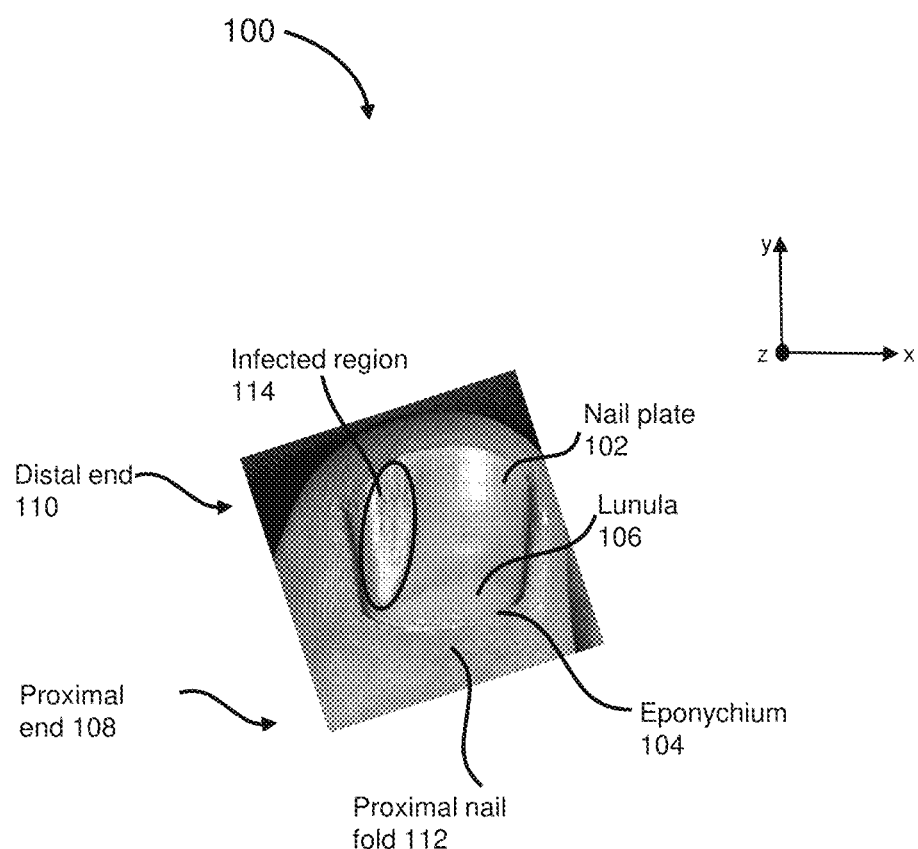
FIG. 1 is an illustration of an exemplary nail apparatus suffering from a fungal infection.

It is noted that the drawings are not necessarily to scale. The drawings are intended to depict only typical aspects of the subject matter disclosed herein, and therefore should not be considered as limiting the scope of the disclosure. Those skilled in the art will understand that the systems, devices, and methods specifically described herein and illustrated in the accompanying drawings are non-limiting exemplary embodiments and that the scope of the present invention is defined solely by the claims.

DETAILED DESCRIPTION

Definitions

Unless otherwise defined, all technical and scientific terms used herein have the same meaning as commonly understood by one of ordinary skill in the art to which this invention belongs. In case of conflict, the present application, including definitions will control.

A "subject" is a vertebrate, including any member of the class mammalia, including humans, domestic and farm animals, and zoo, sports or pet animals, such as mouse, rabbit, pig, sheep, goat, cattle and higher primates.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

In this disclosure, "comprises," "comprising," "containing" and "having" and the like can have the meaning ascribed to them in U.S. Patent law and can mean "includes," "including," and the like, "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Other definitions appear in context throughout this disclosure.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present disclosure.

Embodiments of the disclosure are discussed in detail below with respect to treatment of onychomycosis. However, the disclosed embodiments can be employed for treatment of other medical and/or cosmetic conditions (e.g., fungal infection) without limitation. Examples of fungal infection can include, but are not limited to, onychomycosis.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof can depend at least on the anatomy of the subject in which the systems and devices will be used, the size and shape of components with which the systems and devices will be used, and the methods and procedures in which the systems and devices will be used.

FIG. 1 is an illustration of an exemplary nail apparatus 100 suffering from a fungal infection. The nail apparatus 100 includes a nail plate 102 that is produced by a nail matrix (not shown). The nail plate 102 emerges via proximal nail fold 112 (PNF). The nail plate 102 can be surrounded by a thickened layer of skin called the eponychium 104. The portion of the nail plate 102 adjacent to the PNF (at the proximal end) includes a crescent-shaped region called the lanula 106. The nail plate 102, which is generated by the nail matrix, grows from the proximal end 108 to the distal end 110 of the nail apparatus.

As illustrated in FIG. 1, the nail plate 102 includes an infected region 114 suffering from fungal infection (e.g., onychomycosis). The fungal infection can start from a given region of the nail plate 102 and can spread to other regions of the nail plate 102 (e.g., spread laterally in the x-y plane, spread vertically to various depths along the z-direction, etc.). If the rate of growth of the infected region 114 along the direction of nail growth (along y-direction) is slower than the rate of nail growth, the infected region 114 can be pushed out of the nail plate 102. If the rate of growth of the infected region 114 along the direction of nail growth is faster than the rate of nail growth, the nail plate 102 may continue to remain infected (e.g., infection may spread to lunula). The fungal infection can be treated by reducing the rate of growth of the fungal infection below the rate of nail growth. This can be done, for example, by creating barriers for the growth of fungal infection (e.g., by generating channels in the nail bed) and/or applying topical medication.

FIG. 2A illustrates a cross-section of the nail apparatus 100. The nail plate 102 overlays the nail bed, which includes blood capillaries. The nail plate 102 can be thin (e.g., about 0.25-1 mm), hard, slightly elastic, translucent, convex-shaped and can be made of approximately 80-90 layers of dead, keratinized, flattened cells which are tightly bound to one another via numerous intercellular links, membrane-coating granules, and desmosomes. The nail plate 102 can be divided into a dorsal layer, an intermediate layer and a ventral layer. The dorsal layer can be few cells thick, while the intermediate layer can be softer, more flexible and can represent the thickest layer of the nail plate 102. The ventral layer can be very thin (e.g., it is only about 1-2 cells thick), and it can connect the nail plate 102 to the underlying nail bed.

FIG. 2B illustrates the effects of onychomycosis on a nail apparatus. The nail plate thickens and the layers can separate.

FIG. 2C illustrates an exemplary form of the alteration in the nail apparatus using the nail treatment system to permeabilize the nail plate. The channels shown provide access through the nail plate to the nail bed, but also present access to the nail plate through the sides of the channels.

Figure 2D:
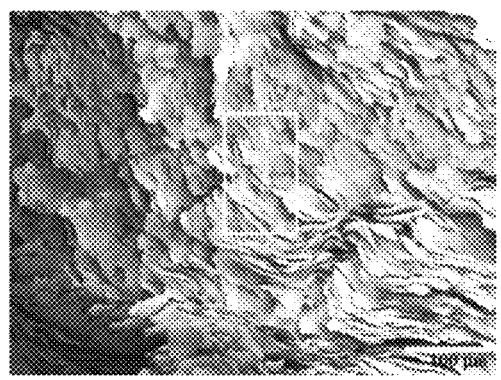
FIG. 2D illustrates how deeply dermatophytes can become embedded within the nail plate structure.

FIG. 2D illustrates how deeply dermatophytes can become embedded within the nail plate 102 structure and how the tiled structure can make it so difficult to deliver solutions to either hyphae or spores. Spores are dormant, surviving for months to years despite the presence of drugs before sprouting to form hyphae again.

The systems and methods for nail treatment described herein provide for an effective and safe treatment of fungal infection of the nail plate 102, which can be successful to improve the cosmetic appearance of the nail. It is understood that such systems and methods may be used for a variety of purposes including, but not limited to, medical, veterinary, cosmetic and aesthetic purposes. This treatment can involve generating channels through the nail plate 102 (e.g., channels extending vertically along the z-axis is shown in FIGS. 1 and 4). A treatment drug (e.g., in liquid, gel or gaseous form) can be added to these channels. This technique can allow the treatment drug to reach portions of the nail plate 102 (e.g., infection regions below the surface of the nail plate 102) that would otherwise not be easily accessible by a treatment drug applied to the surface of the nail plate 102. For example, the channel can serve as a repository of treatment drug that can allow the treatment drug to efficiently diffuse between the different layers of the nail plate 102. The channels can serve as barriers that can reduce the growth rate of fungal infection along the direction of nail growth.

In one implementation, the nail treatment system can include a comprehensive system for the treatment of onychomycosis. The nail treatment system can be configured to provide diagnosis of the fungal infection, access to the fungal infection throughout the nail plate 102 and nail bed below the nail plate 102, delivery of topical anti-fungal drugs, and accelerated nail growth. The nail treatment system can provide access to the infected areas (e.g., via creation of channels through the nail plate 102) using a laser delivering ultraviolet energy (e.g., having wavelength ranging from 100-280 nm, 280-315 nm, 315-400 nm, etc.). After the creation of channels, the nail treatment can deposit anti-fungal drug in the channels.

Figure 3:
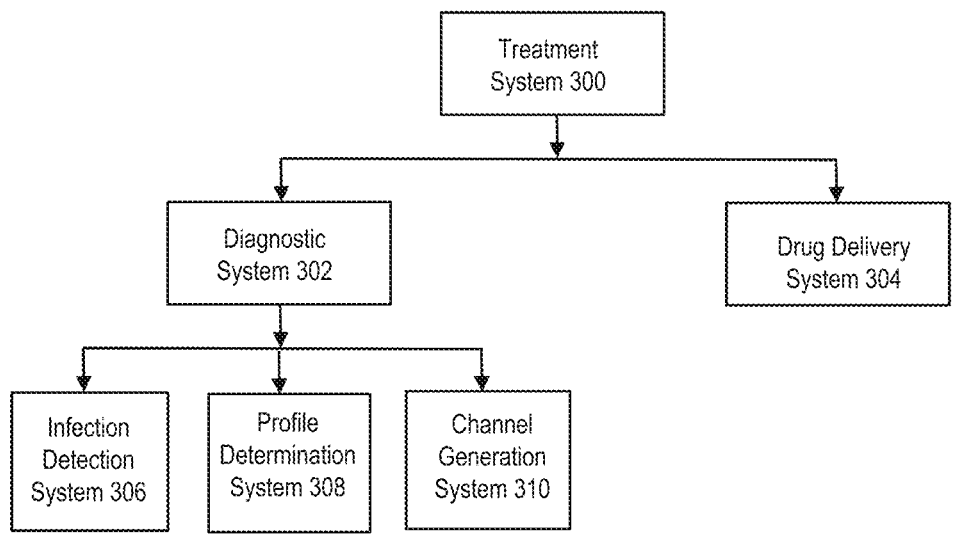
FIG. 3 is a schematic illustration of various sub-systems of an exemplary nail treatment system.

FIG. 3 is a schematic illustration of various sub-systems of an exemplary nail treatment system 300. The nail treatment system can include a diagnostic system 302 and a drug delivery system 304. The diagnostic system 302 can include one or more of an infection detection system 306, profile determination system 308, and channel generation system 310. The infection detection system can detect the nature of the infection and/or region of the nail plate suffering from the infection. The nature of the infection (e.g., type of fungal infection) can be detected by illuminating the nail plate with an input radiation and detecting an output radiation generated/reflected by the nail plate. Based on the detected output radiation (e.g., wavelength of the detected output radiation) the type of fungal infection of the nail plate can be determined. For example, illuminating a given fungus with input radiation of a predetermined wavelength can lead to generation of an output fluorescence signal (e.g. fluorescent spectroscopy). The fluorescent signal (e.g., wavelength of the fluorescent signal) can be compared with a database of fungus fluorescent signals (e.g., by a processor in a controller) to determine the identity of the given fungus. Based on the identity of the fungus, the course of treatment (e.g., type of treatment drug) can be determined.

The fluorescent signal can also be used to determine regions of the nail plate suffering from the infection. For example, a beam of input radiation having a limited lateral extent (e.g., parallel to the nail plate) can be translated over the nail plate. Portions of the nail plate that generate the fluorescent signal can be designated as suffering from fungal infection while regions that do not generate the signal can be designated as free from fungal infection. In some implementations, a camera or sensor (e.g., a charged coupled device (CCD) or a complementary metal-oxide semiconductor (CMOS)) can image the nail plate and an image recognition module can identify the portion of the nail plate suffering from the fungal infection.

The profile determination system can be used to determine the surface profile of the nail plate. This can provide focusing information to the channel generation system and a reference for the pattern generation. The profile can be determined using structured light with a fixed pattern, for example an array of lines. The distortion of the pattern can be used to determine the depth and shape of the surface. Other techniques that can be used to determine the surface profile include interferometry and mechanical scanning using a measuring probe. In some implementations, a grid of lines can be projected onto the surface to be characterized. A camera or sensor can view the lines on the surface and an image processing algorithm can detect deviations from straightness. If the surface (e.g., surface of nail plate) is a plane, then the pattern will be a grid of straight lines, but if there is a contour to the surface the lines will appear to bend. The image processing algorithm can extract the surface profile from the pattern seen on the surface. In some implementations, a focused laser beam can scan the surface. At each point in the scanned path, the focus lens can be moved to ensure that the focused spot is on the nail surface (e.g., using an autofocus mechanism). The distance the focus lens is moved at various locations can indicate the surface profile. In some implementations, interferometry (e.g., optical coherence tomography) can be used to determine the surface profile. For example, a plane electromagnetic wave projected on the nail can interfere with the incident and the reflected beam. This can allow for detection of the phase shifts corresponding to the contour of the nail (e.g., different path lengths). In some implementations, confocal microscopy can be used to determine the surface profile of the nail plate.

The channel generation system can generate channels through the nail plate (e.g., channels extending vertically along the z-axis as shown in FIG. 2C). This can be done, for example, by illuminating the nail plate with a laser beam and directing the laser beam to portions of the nail plate (e.g., by scanning) where it is desirable to generate a channel. Scanning can be performed using a galvanometer to move the beam or by physically moving the optics used to modify the beam (e.g., redirect, focus, or collimate). The channels may be produced in any number of desirable patterns (e.g., rectilinear patterns, circular patterns, hexagonal, etc.) which can be used to adjust the channel density. In addition, the density of channels (e.g., number of channels per unit area) can vary in different regions of the nail plate (e.g., along the length of the nail plate). For example, portions of the nail plate with higher concentration of fungal infection can be treated to include higher concentration of channels.

Figure 4A:
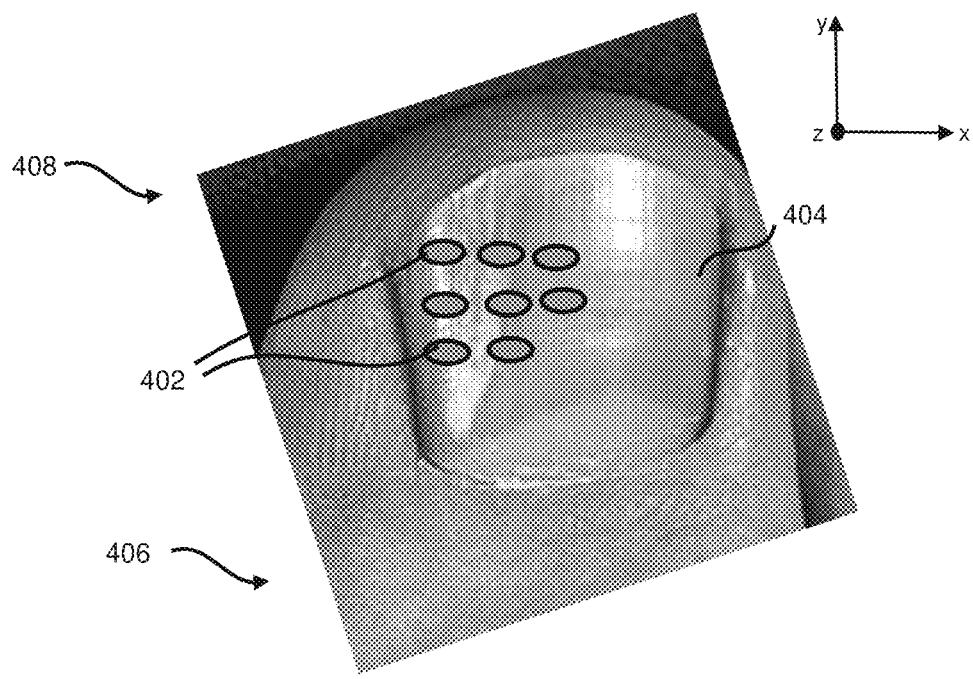
FIG. 4A illustrates an exemplary arrangement of channels in a nail plate.

Individual channels may be produced in various geometries. For example, a cross-section of the channel (e.g., cross-section parallel to the surface of the nail plate) can have a rectangular shape, a circular shape, an oval shape and the like. FIG. 4A illustrates an exemplary arrangement of channels 402 having oval shaped cross-sections. As shown, the channel cross-section is smaller along the direction of growth of the nail plate 404 (e.g., along the y-axis from the proximal end 406 to the distal end 408) and longer along the direction lateral to the direction of growth of the nail plate (e.g., along the x-axis). In some implementations, such a cross-section geometry can be desirable. For example, fungal infections can spread faster along the direction of growth of the nail plate compared to the lateral direction. Channels with oval shaped cross-section geometry (or other geometries elongated along the direction lateral to the direction of nail grown) shown in FIG. 4A can reduce the spread of fungal infection along the direction of growth of the nail plate. If the rate of growth of the fungal infection is slower than the rate of growth of the nail plate (e.g., from the proximal end 406 to the distal end 408), the fungal infection can be expelled by the growing nail plate.

The shape/size of the cross-section can vary along the depth of the nail plate. The shape and size of a desired channel can be determined based on the nature of fungal infection, volume of treatment drug needed for treatment of the fungal infection, etc. The depth of the channel can be based on the energy of each laser pulse and the number of pulses, effectively the time of exposure of the nail plate to the laser beam. In some implementations, the channel generation system can include a feedback mechanism to determine the depth of the channel. For example, it can be desirable to configure the channel to completely extend through the nail plate to the nail bed (e.g., along the z-axis through the various layers of the nail plate). Such a feedback mechanism can prevent the laser beam from damaging the nail bed by detecting a fluorescence signal that is generated when the laser beam interacts with the nail bed (e.g., blood vessels in the nail bed). In some implementations, the channel generation system can include a camera or sensor configured to detect the fluorescent signal generated by the interaction between the laser beam and the nail bed. Upon detection of the fluorescent signal, the source generating the laser beam can be turned off. This can prevent damage of the nail bed.

In some implementations, multiple sub-beams can be simultaneously generated by illuminating a mask with a large laser beam. The multiple sub-beams can simultaneously generate multiple channels. In one implementation, a high power, broad beam excimer laser operating at 248 nm can be used with a mask projection to produce patterned channel features. The laser can illuminate the mask, and the portion of the laser beam that passes through the mask is then sent through a lens which can reduce the size of the image on the target.

Figure 4B:
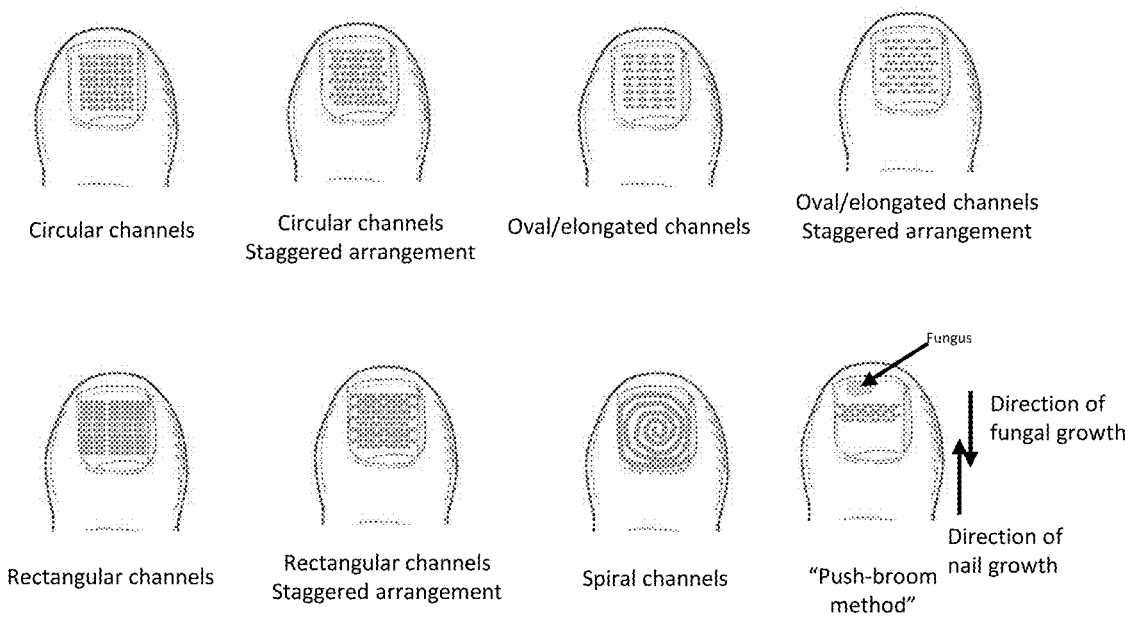
FIG. 4B illustrates exemplary shapes and arrangements of channels in nail plates.

FIG. 4B illustrates exemplary arrangements and shapes of channels on the nail plate. As illustrated the channels can be circular, oval (or elongated), rectangular, spiral in shape. The channels can be arranged in a staggered arrangement, rectangular grid, etc. The nail grows outward towards the distal end while fungal infection originates from the distal end of the nail and migrates backwards towards the proximal end. Fungi exist in two forms: 1) hyphae, the active form, and 2) spores, the dormant form. Fungi reproduce through spores. Hyphae consume keratin in the nail plate which causes the nail plate to spread and appear to thicken. Drugs are effective in treating fungal infection in the active, hyphae form, but are ineffective in treating spores. An initial drug application may treat hyphae, but remaining spores will germinate to form hyphae.

One exemplary form of the treatment shown in FIG. 4B is referred to as the "push-broom method." Staggering channels can provide an obstacle to fungal growth. Hyphae move through the nail plate. Staggered, channels force to hyphae to migrate around the periphery of the channels as illustrated. This can slow the effective linear rate of fungal migration. If the rate of nail growth exceeds the rate of fungal migration, nails may be able to expel the fungus. Filling the channels with a drug can also improve the effectiveness of this approach.

FIG. 5A illustrates a scanning electronic microscopic (SEM) image of an exemplary array of channels generated by the above-mentioned laser-mask setup. The channels are generated using a 19×19 hole array mask. The channels can have an average entrance diameter of ~35 micrometers, and can have a depth of about 300 micrometers. FIG. 5B illustrates a magnified version of the image in FIG. 5A.

Figure 6A:
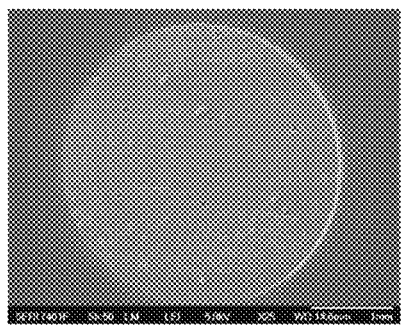
FIG. 6A illustrates a scanning electronic microscopic (SEM) image of another exemplary array of channels in a nail plate.
Figure 6B:
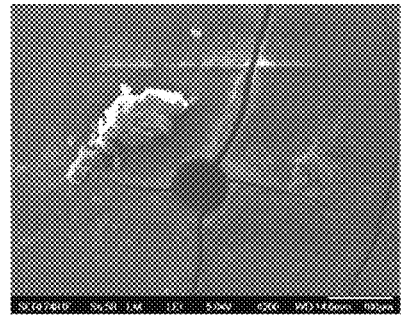
FIG. 6B illustrates a magnified version of the image in FIG. 6A.

FIG. 6A illustrates a scanning electronic microscopic (SEM) image of another exemplary array of channels generated by the excimer laser. The channels are generated using a 3×2 hole array mask. The channels can have an average entrance diameter of about ~75 micrometers. FIG. 6B illustrates a magnified version of the image in FIG. 6A.

Figure 6C:
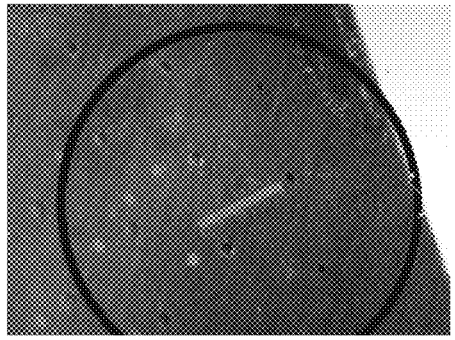
FIG. 6C illustrates an exemplary micrograph of an array of micro-channels generated in a model nail generated using a pulsed Nd:YAG laser.

FIG. 6C illustrates an exemplary photo-micrograph of an array of micro-channels generated in a model nail generated using a pulsed Nd:YAG laser generating light at 266 nm focused through a microlens array. The channels can have a diameter of about 50-70 micrometers.

Figure 7:
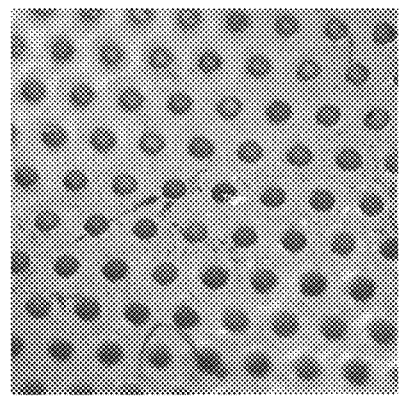
FIG. 7 illustrates a photo-micrograph of an exemplary array of channels generated by scanning a DPSS laser beam.

In one implementation, a diode-pumped solid-state (DPSS) laser operating at 355 nm can be used to generate the channels. FIG. 7 illustrates a photo-micrograph of an exemplary array of channels generated by scanning the DPSS laser beam. The channels can have an average entrance diameter of ~70 micrometers. The spot size of the DPSS laser (e.g., using a focusing optic having a numerical aperture (NA) of 0.1) can be 4.3 micrometers in diameter. A channel having a diameter of about 70 micrometers can be generated by moving the laser beam in an area having 70 micrometer diameter.

In some implementations, the laser beam can be an ultraviolet laser (e.g., having wavelength in the range of about 100-280 nm, 280-315 nm, 315-400 nm, etc.). In some implementations, the laser beam can be generated by one or more of excimer lasers (e.g., operating at 157 nm, 193 nm, 248 nm, 308 nm, and 351 nm, etc.), a DPSS laser (e.g., operating at 213 nm, 266 nm, 355 nm, etc.), and other laser systems that generate UV light. The width of the laser beam (e.g., in the Rayleigh length of a Gaussian beam) can be less than about 100 micrometers.

Figure 16:
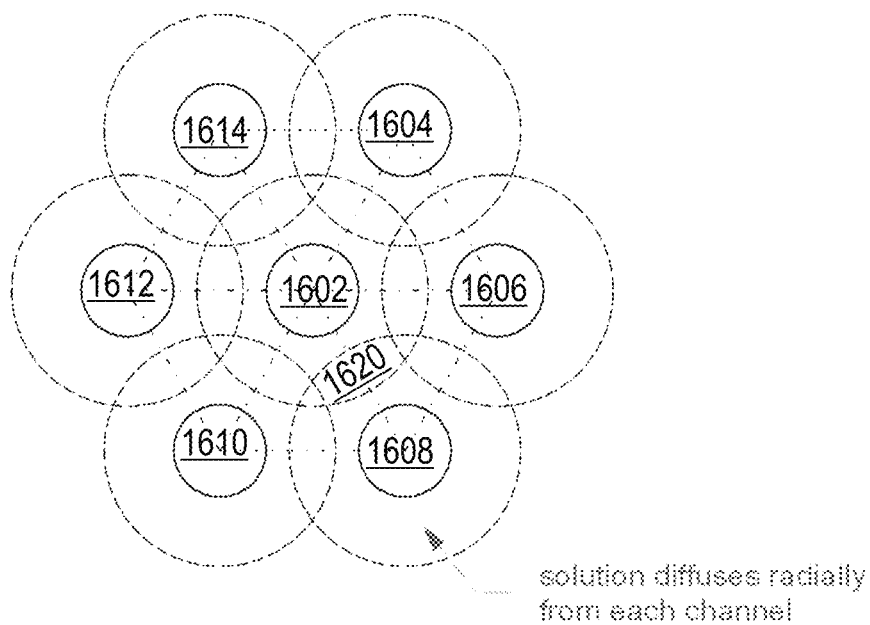
FIG. 16 illustrates exemplary overlapping influence of treatment drugs from various channels.

Using an ultraviolet wavelength laser beam for generating channels can have several advantages over using longer wavelength laser beam (e.g., $CO_2$ laser). For example, a shorter wavelength laser beam can generate channels having finer features (e.g., a smaller diameter). It can be desirable to generate channels having finer features because it can allow for greater area of contact between the treatment drug (e.g., deposited in the channels) and the nail plate. Smaller holes can allow for a higher channel packing density with a greater effective surface area while sparing the structural integrity of the nail as compared to larger holes. This can improve the distribution treatment drugs (e.g., via diffusion through the nail plate) in the nail plate (e.g., at various depths of the nail plate), and can allow for overlapping zones of influence of treatment drugs (e.g., from treatment drugs in adjacent channels) as illustrated in FIG. 16.

The mechanism of channel generation by lasers operating in the UV range can be different than those generated by lasers having longer wavelengths (e.g., visible, infrared, etc.). For example, UV lasers can break molecular bonds and prevent reduce heat generation during channel generation. Lasers operating at larger wavelengths (visible or infrared) can generate channels through intense heating of the nail plate. The generated heat can spread in all directions and can damage undesired portions of the nail plate. The size of the waist of a focused laser beam varies proportionally with the laser wavelength (e.g., larger the laser wavelength, larger the beam waist). In other words, a laser operating in the UV range can produce smaller focused beams than lasers with higher wavelengths. Therefore, using UV lasers can allow for better control of the shape of the channels while preventing thermal damage to undesired portions of the nail plate.

In some implementations, channels can be generated using one or more needles (e.g., array of heated needles). The needle (or array of heated needles) can be coupled to an actuator that can move the heated needle over the nail plate to the desirable location (e.g., infected portion of the nail plate). In some implementations, the needle can be heated which can allow the needle to generate a channel with relative ease.

The nail treatment system can include a drug delivery system for depositing treatment drugs (e.g. topical drugs) into the channels. In some implementations, treatment drugs can be delivered using a combination of vacuum and pressure. The treatment drug can be in liquid phase, a gaseous phase, or a combination thereof. The treatment drug can be deposited in the channel by a drug depositing mechanism (e.g., a sprayer or a syringe) that can expel the tropical drug (e.g., at a positive pressure) into the channels.

In some implementations, nail plate properties can be modified prior to/during deposition of treatment drugs. For example, chemical enhancers (e.g., keratolyics such as papain, urea, and salicylic acid; mercaptans (N-[2-mercaptopropionyl] glycine, zinc and sodium pyrithone, 8-mercaptomenthone, meso-2,3-dimercapto succinic acid), sodium metabisulphite, keratolytic agents (salicylic acid, urea, guanidine hydrochloride); etc.) can be applied to the nail plate prior to the deposition of treatment drug. In some implementations, iontophoresis, and ultrasound can be applied to the nail plate to improve the deposition of treatment drug in die channels.

Figure 8:
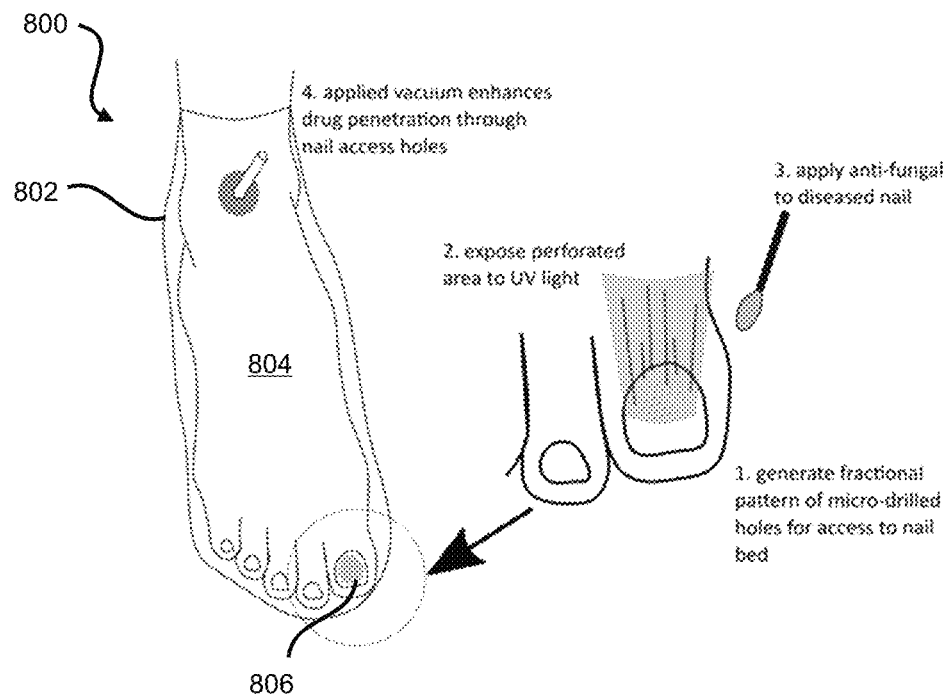
FIG. 8 illustrates an exemplary system for enhancing drug delivery.

Forcing the treatment drug into the channels can create a pressure increase since the air sealed within the channels and nail may not escape. This pressure increase can resist drug injection into the holes and can prevent complete delivery (e.g., delivery of treatment drug at certain depths). However, generating a vacuum to remove air before and/or during delivery can enhance the drug penetration. Subsequent pressure could further enhance delivery. FIG. 8 illustrates an exemplary system 800 for enhancing drug delivery. As illustrated, the drug delivery system includes a chamber 802 (e.g., sealed bag or other such chamber) configured to receive the foot 804 with the infected nail plate 806. After initial treatment of the nail plate 806 (e.g., generation of channels in the nail plate (e.g., using a UV laser beam)), exposing the nail to UV light, and application of treatment drug) the foot can be placed in the chamber. The chamber 802 can be sealed, and a vacuum pressure can be generated in the chamber (e.g., by using a vacuum pump). This vacuum pressure can force the treatment drug into the channels. In some implementations, longitudinal waves (e.g., ultrasound) can drive the treatment drug into the channels. For example, a Q-switched laser pulse incident on the surface of the nail can generate a wave (e.g., shock wave) in the nail plate that can drive the drug into the channels. In some implementations, the nail plate 806 can be heated to an elevated temperature to increase the diffusion rate of the treatment drug through the nail plate.

In some implementations, the nail plate can be sealed after treatment drug deposition. For example, after deposition of treatment drug in the channel, a sealant can be applied on the surface of the nail plate which can prevent the treatment drug from leaving the channels. This can make the channels produced in the nail plate a closed reservoir and can allow the treatment drug to diffuse into the nail plate over a long period of time.

Figure 9:
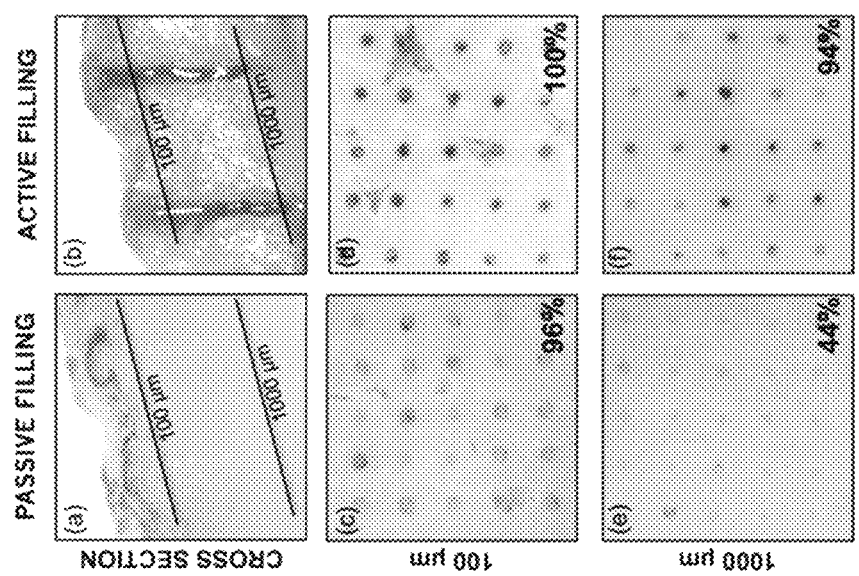
FIG. 9 includes exemplary images illustrating the effect of vacuum and pressure to enhance drug delivery in laser drilled channels.

In some implementations, a vacuum of about −1 atm followed by delivery of PEG400 at a pressure of about 1 atm can increase the delivery of the treatment drug. FIG. 9 shows PEG400 being delivered to porcine skin mounted in a Franz cell. Active filling was performed by subjecting the sample to applying a 3-minute cycle of pressure (1 minute, +1.0 atm), vacuum (1 minute, −1.0 atm), and pressure (1 minute, +1.0 atm).

Figure 10:
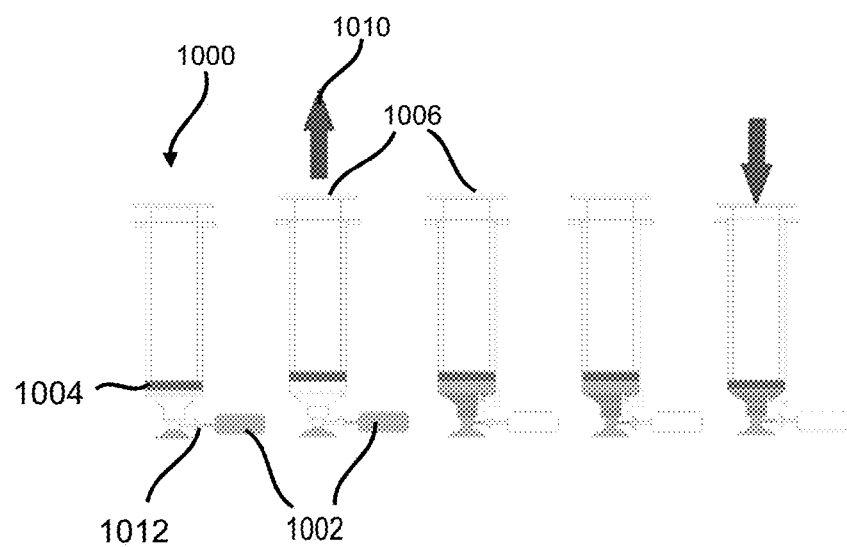
FIG. 10 illustrates exemplary embodiments of a drug delivery system.

FIG. 10 illustrates exemplary embodiments of a drug delivery system 1000. The treatment drug (e.g., in liquid phase) can be contained in a disposable unit dose package 1002 (e.g., a plastic ampule attached to a syringe with a valve). A compliant, sealing tip 1004 can be at the end of the syringe 1006 configured to drive treatment drug out of the package 1002. A vacuum can be generated by retracting the syringe 1006 in direction 1010. The valve can then be opened to allow the drug to flow into the tip, after which the valve 1012 can be closed. The treatment drug can be delivered under pressure by depressing the syringe 1006. In some implementations, a vacuum/pressure can be created by a hand pump, an electrically driven vacuum/pressure pump, etc. Alternate approaches include enclosing the toe, foot, or any other portion of the body including the nail to allow the application of pressure/vacuum.

The treatment drug can include any appropriate antifungal drug approved for the treatment of onychomycosis in liquid form (e.g., Efinaconazole topical solution (Jublia), Ciclopirox (Penlac), Tavaborole (Kerydin), etc.). Other treatment drugs can include one or more drugs with the following drug tradenames (generic drug names): Blis-To-Sol Powder (undecylenic acid), Extina (Pro) (ketoconazole), Mycostatin Topical (Pro) (nystatin), Naftin (Pro) (naftifine), Nizoral Topical (Pro) (ketoconazole), Nyamyc (Pro) (nystatin), Tinactin (tolnaftate), Zeasorb-AF (miconazole), Zeasorb-AF Drying Gel (miconazole), Vusion (Pro) (miconazole/zinc oxide), Spectazole (Pro) (econazole), Loprox (Pro) (ciclopirox), Lotrimin AF Athlete's Foot Powder (miconazole), Oxistat (Pro) (oxiconazole), Pedi-Dri (Pro) (nystatin), Penlac (Pro) (ciclopirox), Xolegel (Pro) (ketoconazole), Ertaczo (Pro) (sertaconazole), Nizoral Shampoo (ketoconazole), Nizoral A-D (ketoconazole), Jublia (Pro) (efinaconazole), Nystop (Pro) (nystatin), Penlac Nail Lacquer (ciclopirox), Lamisil AT (Pro) (terbinafine 6), Kerydin (Pro) (tavaborole), Pedipirox-4 (ciclopirox), Dermagran AF (miconazole), Fungi-Nail (undecylenic acid), M-Zole 3 (miconazole), Absorbine Athlete's Foot (tolnaftate), Absorbine Jr Antifungal (tolnaftate), Aftate (tolnaftate), Aloe Vesta (miconazole), Athletes Foot Cream (terbinafine), Azolen (miconazole), Baza Antifungal (miconazole), Blis-To-Sol (tolnaftate), Canesten (clotrimazole 2), Clarus Antifungal (tolnaftate), CNL8 Nail (Pro) (ciclopirox), Critic-Aid Clear AF (miconazole), Cruex (undecylenic acid), Cruex Prescription Strength (Miconazole), DermaFungal (miconazole), Desenex Antifungal Atheletes Foot Spray Liquid (miconazole), Desenex Antifungal Cream (clotrimazole), Desenex Antifungal Foot Cream (miconazole), Desenex Jock Itch (miconazole), Ecoza (Pro) (econazole), Elon Dual Defense Anti-Fungal Formula (undecylenic acid), Exelderm (Pro) (sulconazole), Exoderm (salicylic acid/sodium thiosulfate), Fungi-Guard (tolnaftate), FungiCURE Pump Spray (clotrimazole), Fungoid (miconazole), Ketodan (Pro) (ketoconazole), Kuric (ketoconazole), Lamisil AF Defense (tolnaftate), Lamisil AT Cream (terbinafine), Lamisil AT Cream for Jock Itch (Pro) (terbinafine), Lamisil AT Spray (Pro) (terbinafine), Loprox TS (ciclopirox), Lotrimin AF Athlete's Foot Cream (clotrimazole), Lotrimin AF Deodorant Powder Spray (miconazole), Lotrimin AF Jock Itch Powder Spray (miconazole), Lotrimin Ultra Athlete's Foot Cream (butenafine), Luzu (Pro) (luliconazole), Mentax (Pro)(butenafine), Micaderm (miconazole), Micatin (miconazole), Micro-Guard (miconazole), Miranel AF (miconazole), Mitrazol (miconazole), Monistat-Derm (Pro) (miconazole), Mycelex (Pro) (clotrimazole), Mycocide NS (tolnaftate), Myco Nail A (undecylenic acid), Naftin-MP (naftifine), NuZole (miconazole), Nyata (nystatin), Ony-Clear (miconazole), Pediaderm AF (Pro) (nystatin), Podactin (tolnaftate), Q-Naftate (tolnaftate), Rash Relief Antifungal (miconazole/zinc oxide), Secura Antifungal (miconazole), Secura Antifungal Extra Thick (miconazole), Soothe & Cool Inzo (miconazole), Tetterine (miconazole), Tinactin Jock itch (tolnaftate), Tinaderm (tolnaftate), Tinamar (tolnaftate), Tinaspore (tolnaftate), Ting (tolnaftate), Triple Paste AF (miconazole), Undelenic (undecylenic acid), Versiclear (salicylic acid/sodium thiosulate).

The channels can provide sustained access to the infected areas, and the treatment drug delivered through the channels can provide for clearance of the fungal infection. The fungal infection can exist in two forms: spores and hyphae (that sprout from spores). In some implementations, the treatment system can allow for repeated treatments to address new hyphae arising from the spores. Treatment drug delivered into the channels can diffuse radially as well as axially into the nail plate to produce a zone of influence around each channel. Closely spacing the channels can result in overlapping zones of influence for maximum coverage. In some implementations, the spacing between the channels can be determined based on the treatment drug (e.g., diffusion properties of the treatment drug).

Figure 11A:
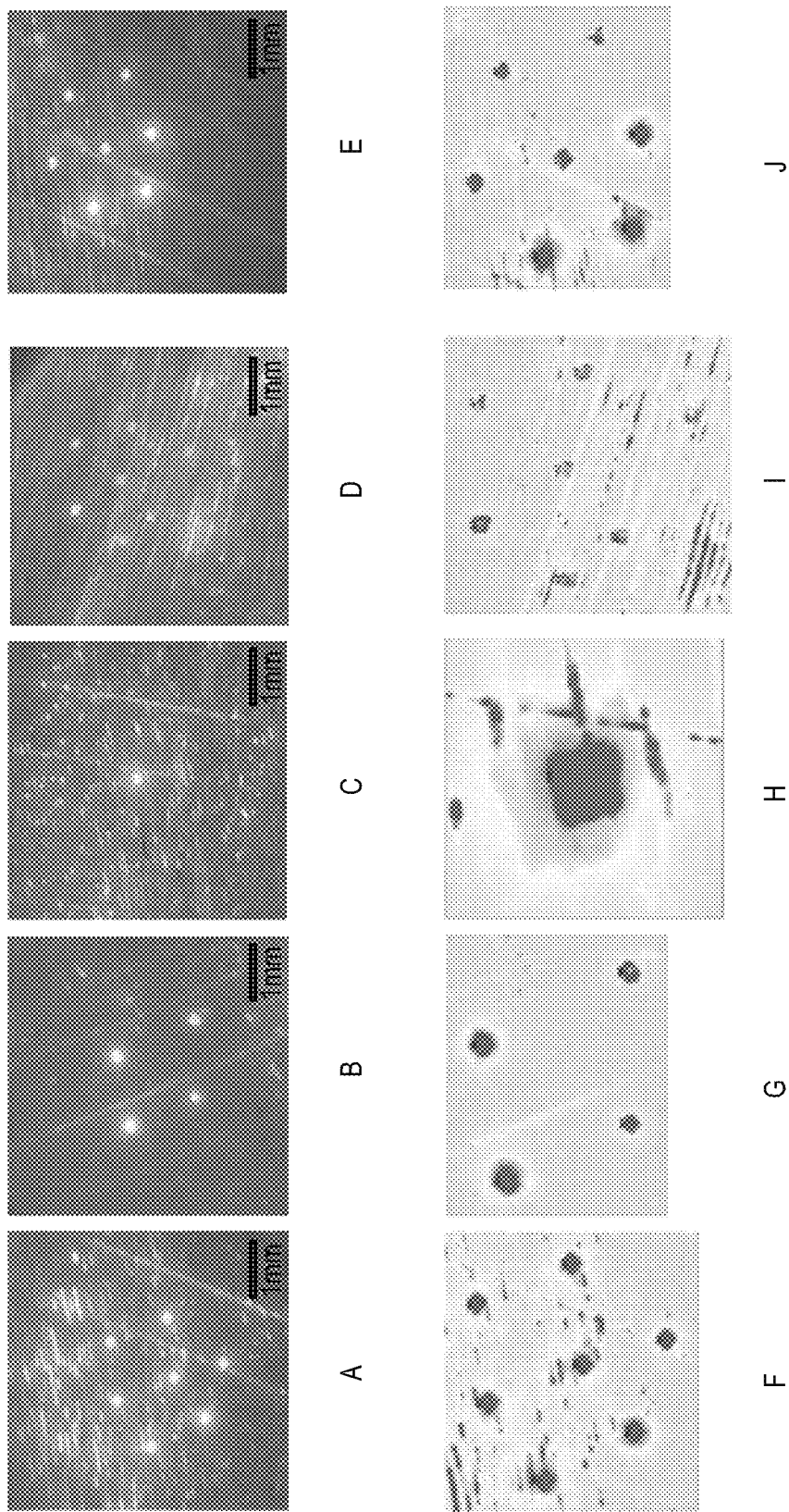
FIGS. 11A-11B illustrate exemplary images of penetration of calcein dye.
Figure 11B:
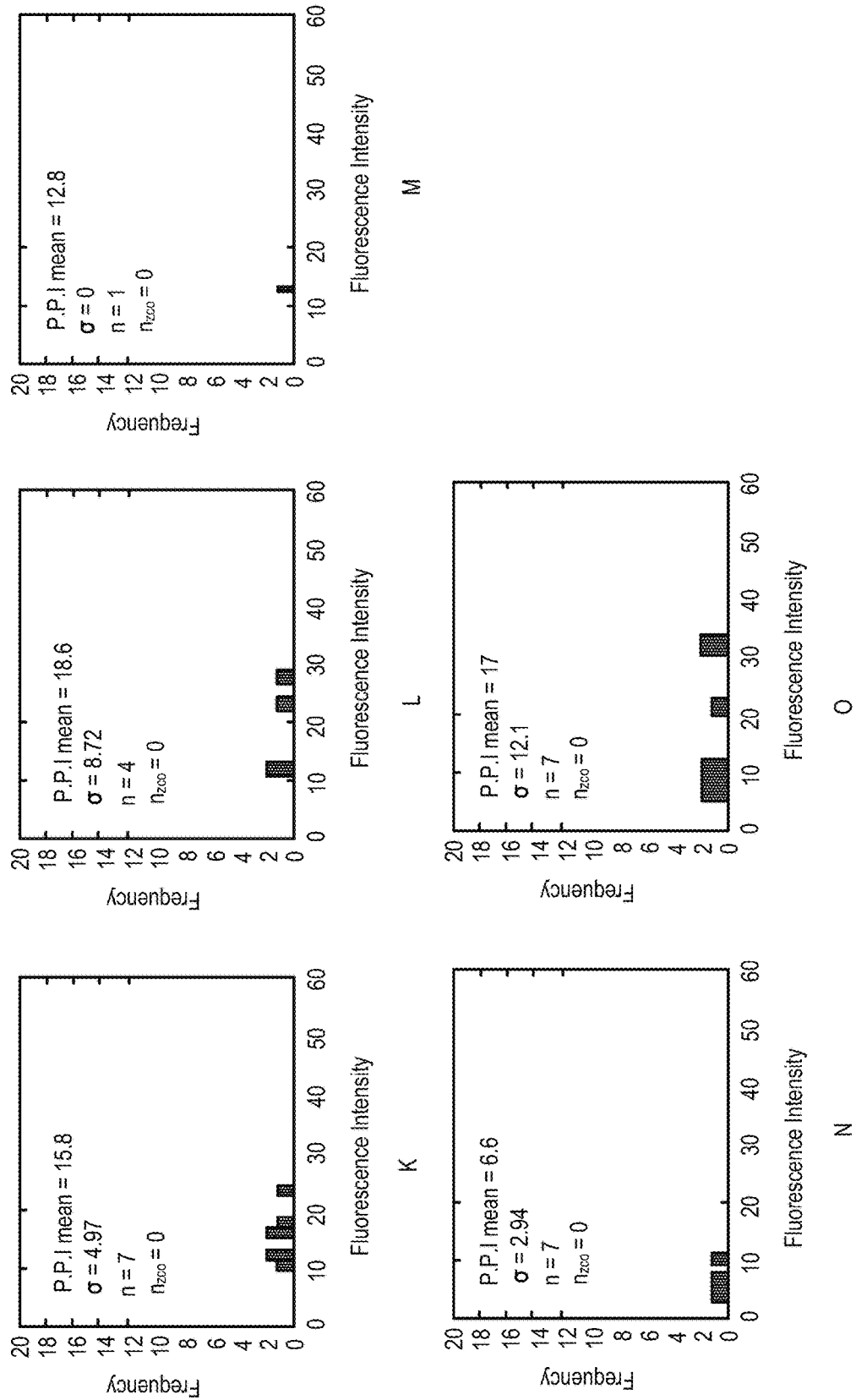

FIG. 11 illustrates exemplary images of penetration of a calcein dye from channels produced using a 2940 nm Er:YAG laser. The channels have a diameter of approximately 0.29 mm (290 micrometers). The images were obtained using fluorescent confocal microscopy and intensity varies with dye penetration. As the images show, the calcein dye penetrates radially from the edge of each channel.

In one implementation, physical diffusion through a model nail material around the channels can be evaluated using a dye solution including Alexa Fluor 405 mixed with dimethyl sulfoxide (DMSO), which is an organic solvent. Alexa Fluor 405 is a fluorescent probe formulated for use in two-photon excitation microscopy, and it can allow for visualization of the dye solution distribution through the model nail in three dimensions (lateral and through-thickness) using a two-photon excitation microscope.

FIGS. 12A and 12B are photo-micrographs illustrating exemplary delivery of a dye solution (e.g., dye solution including Alexa Fluor 405 mixed with DMSO) through micro-channels (generated using excimer laser) throughout the model nail. The dye solution can be applied to the surface of the samples and be allowed to sit for approximately 30 minutes. The photo-micrograph in FIG. 12A illustrates an image of a channel in the model nail (e.g., produced using the excimer laser with a single hole mask) and 790 nm excitation source. The image is filtered to enhance dye fluorescence. FIG. 12A illustrates that there is little lateral penetration in the nail. Serial images through the thickness of the nail plate have also showed little fluorescence. This indicates that there is little penetration into the nail. The photo-micrograph of FIG. 12B illustrates an image the channel in the model nail generated without an optical filter.

Figure 13A:
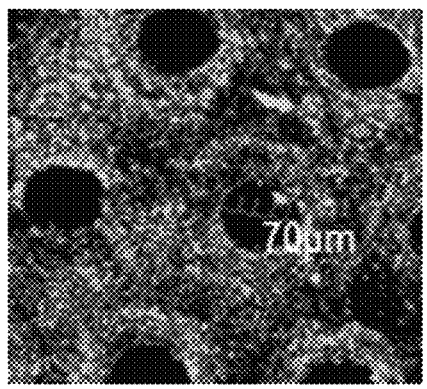
FIGS. 13A and 13B are micrographs illustrating exemplary effect of vacuum/pressure on delivery of the dye solution through micro-channels generated using DPSS laser.
Figure 13B:
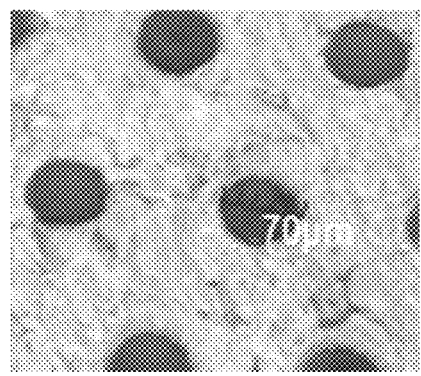

FIGS. 13A and 13B are photo-micrographs illustrating exemplary effect of vacuum/pressure on delivery of the dye solution through micro-channels (generated using a DPSS laser) through the model nail ("sample"). The dye solution including Alexa Fluor 405 mixed with dimethyl sulfoxide (DMSO) can be applied to the surface of the sample and the sample can then be placed in a vacuum chamber under vacuum (~25 in Hg) (e.g., for about one minute). The vacuum can be released, and more dye can be applied to the sample. This process can be repeated for approximately 30 minutes.

The photo-micrograph in FIG. 13A illustrates an image of a channel in the model nail (e.g., produced using the DPSS laser with a single hole mask) and 790 nm excitation source. The image is filtered to enhance dye fluorescence. FIG. 13A illustrates there is substantial fluorescence, both around each hole as well as between holes. This indicates that there was increased penetration into the nail compared to FIGS. 12A and 12B. The photo-micrograph of FIG. 13B illustrates an image the channel in the model nail generated without an optical filter.

Figure 14:
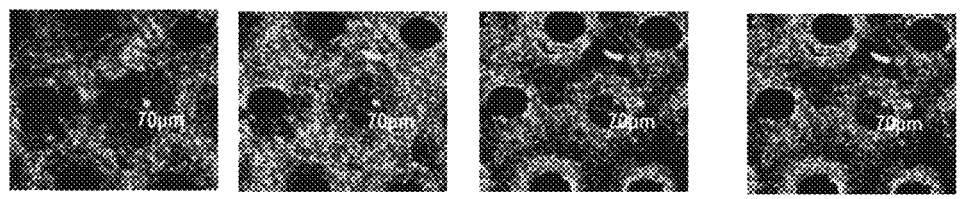
FIG. 14 illustrates images of cross-section of the sample in FIG. 13A at various depths.

FIG. 14 illustrates images of cross-sections of the sample at various depths. The fluorescence in the images indicate that the dye penetrated through the thickness. The images illustrate the distribution over a depth of 30 micrometers.

Figure 15:
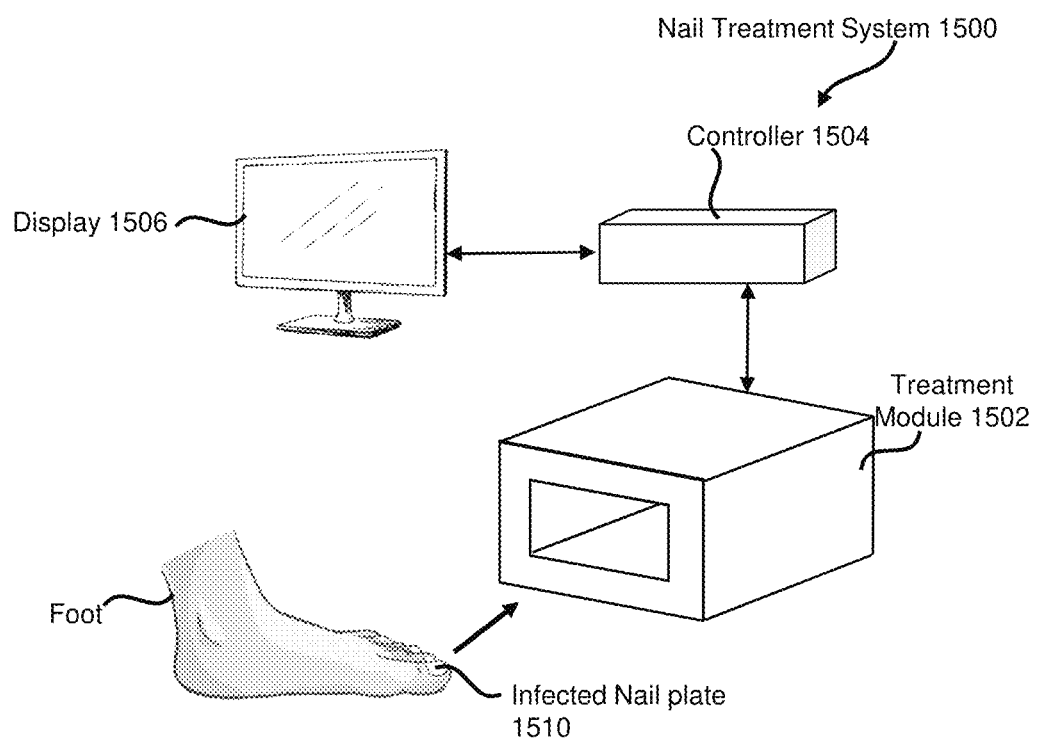
FIG. 15 is an illustration of an exemplary embodiment of a treatment system for treating fungal infection of a nail plate.

FIG. 15 is an illustration of an exemplary embodiment of a nail treatment system 1500 for treating fungal infection of a nail plate 1510. The nail treatment system can include a treatment module 1502, a controller 1504, and a display 1506. The treatment module 1502 can be configured to receive the foot with the infected nail plate. The treatment module 1502 can include one or more of an infection detection system, profile determination system, channel generation system and drug delivery system. A user can select a desirable treatment operation (e.g., detection of infection, determination of nail profile, generation of channels, delivering drug in the channel etc.) via an interface in the display 1506.

In one implementation, the interface can instruct the user to place a subject's foot in the treatment module 1502. The controller 1504 can detect that the foot has been placed in the treatment module (e.g., via pressure sensors in the treatment module), and can present icons indicative of the various treatment options available to the user. The controller 1504 can receive a user selection from the display 1506 and can instruct the treatment module to carry out the procedure. For example, the controller 1504 can instruct the infection detection system in the treatment module 1502 to carry out fluorescence spectroscopy of the fungal infection, generate channels etc. Based on the detected fluorescence image, the controller 1504 can identify the fungal infection and present this information on the display 1506. In some implementations, the controller 1504 can also provide various treatment options (e.g., characteristics of recommended channels, treatment drugs) to the user. The user can select one or more treatment options. Based on the user selection the controller 1504 can instruct the treatment module 1502 to carry out the next treatment operations. Some implementations of the nail treatment system can include separate treatment modules for the various treatment operations.

FIG. 16 illustrates exemplary overlapping influence of treatment drugs from various channels 1602-1614. The active treatment drug deposited in these channels can diffuse outwards (e.g., along concentric rings) from the channels. This can result inportions of the nail plate (e.g., region 1620) that can receive treatment drugs from multiple channels (e.g., from channels 1602 and 1608).

Figure 17:
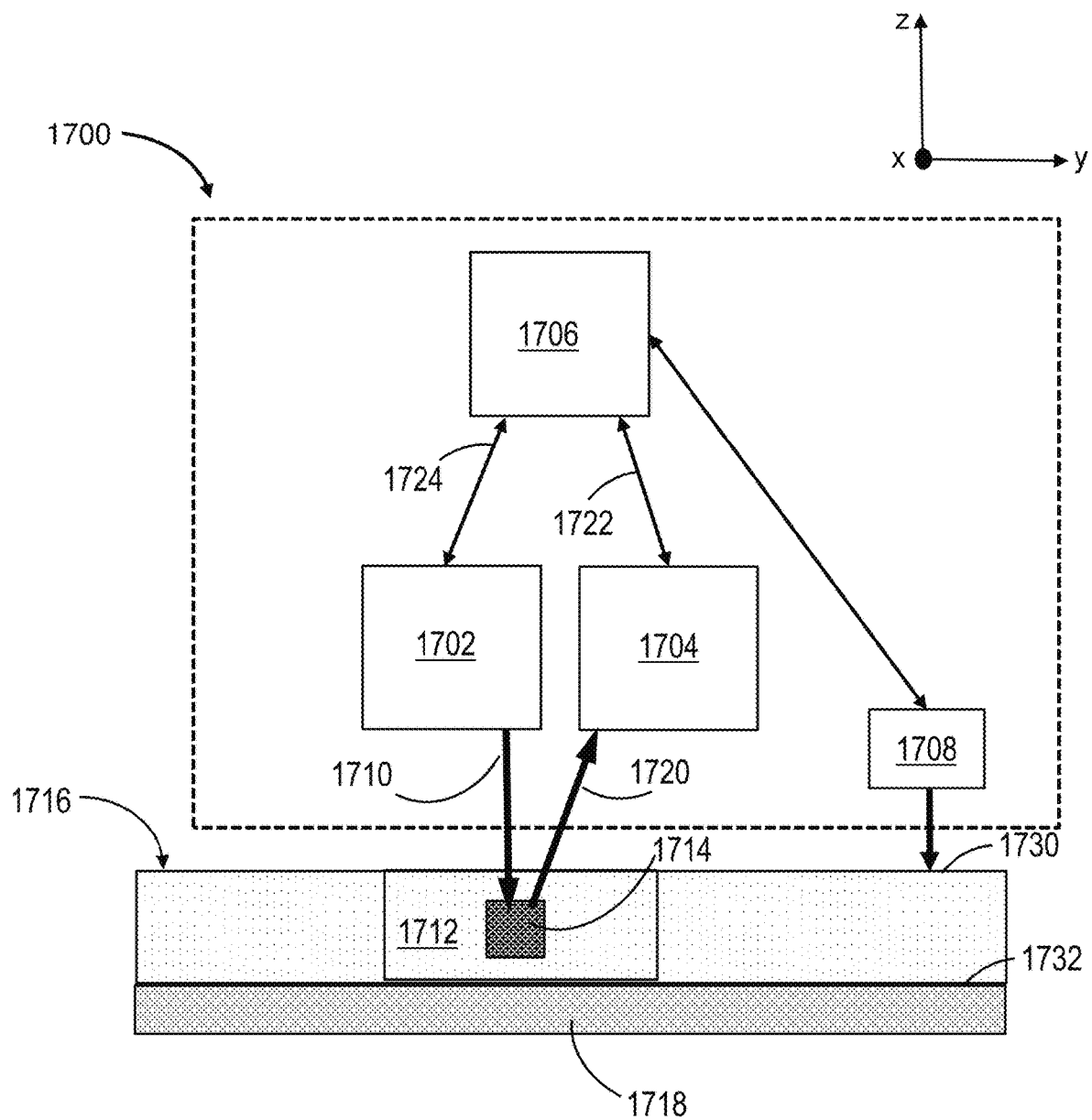
FIG. 17 illustrates an exemplary treatment system.

In one implementation, such as illustrated in FIG. 17, a treatment system 1700 (or treatment system 300) can include a channel generation system 1702 (or channel generation system 310) configured to expose an infected region of a target tissue with a laser beam traveling along an optical axis. For example, as illustrated in FIG. 17, the channel generation system 1702 can direct a laser beam 1710 to an infected region 1712 of a target tissue 1716 (e.g., a nail plate). The laser beam 1710 can be focused at a focal volume 1714 located in or adjacent to the target tissue 1716 (e.g., above the target tissue, in the target tissue, at the surface of the target tissue, etc.). In some implementations, the laser beam 1710 can have a wavelength ranging from about 100 nm to about 400 nm. The laser beam 1710 can generate one or more channels (e.g., a first channel) in the infected region 1712.

The channel generation system 1702 can generate one or more channels adjacent to the first channel (e.g., as illustrated in FIG. 16). These channels can extend from a proximal end 1730 to a distal end 1732 which is next to an adjacent tissue 1718 (e.g., a nail bed tissue). The first channel and one or more of the adjacent channels can receive an active treatment agent. The active treatment agent in the channels can diffuse to diffuse to portions of the target tissue adjacent to the channels. For example, as illustrated in FIG. 16, solution can diffuse radially from each channel and create overlapping zones of influence from the channels. This can allow for coverage of active treatment agents to regions between the channels (e.g., between the first channel and a second channel adjacent to the first channel). In some implementations, the treatment system 1700 can include a drilling system (not shown) for generating/drilling channels (or holes) in the target tissue 1716.

The treatment system 1700 can include a controller 1706 configured to receive a first detection signal 1722 from the detection system 1704 indicative of the detected radiation 1720. The controller 1706 can determine the identity of the fungi coupled to the infected region 1712 in the target tissue 1716 based on the signal 1722 (which in turn is indicative of the detected radiation 1720). In some implementations, the treatment system 1700 can include a driving system 1708 configured to drive the active treatment agent in channels that have been generated in the target tissue 1716 (e.g., by the laser beam 1710, drilling system, etc.). This can be done, for example, by application of modulated pressure waves, application of heat, application of an ultrasound wave, etc., to the target tissue 1716. In some implementations, the modulated pressure wave can be generated by directing a second laser beam on the target tissue 1716. In some implementations, the controller 1706 can detect a depth associated with the first channel using at least one of reflectance confocal microscopy and optical coherence tomography.

The treatment system 1700 can include a detection system 1704 configured to detect a radiation 1720 generated by one or more of the target tissue 1716, a fungi coupled to the infected region 1712 in the target tissue 1716, and an adjacent tissue 1718 (e.g., a nail bed) located proximal to the target tissue 1716 as a result of interaction with the laser beam 1710. The radiation 1720 can include one or more of a fluorescence from the fungi, a fluorophore (e.g., 5-ALA, an ester of ALA, and ppIX) coupled to the fungi, etc. In some implementations, radiation 1720 can include can include radiation ("second radiation") generated by the interaction between the laser beam 1710 and the adjacent tissue 1718 (e.g., when the first channel extends to the adjacent tissue 1718 from the proximal surface 1730).

The detection system 1704 can be configured to detect the second radiation and transmit a second detection signal (e.g., included in the detection signal 1722) indicative of interaction between the laser beam 1710 and the adjacent tissue 1718 (e.g., nail bed tissue). In some implementations, the controller 1706 can determine based on the second detection signal that the first channel has reached the adjacent tissue 1718. Based on this determination, controller 1706 can send a control signal 1724 to the channel generation system 1702. Based on the control signal 1724, the channel generation system 1702 can terminate interaction between the laser beam 1710 and the target tissue 1716 and/or the adjacent tissue 1718. For example, the channel generation system 1702 can stop the generation of the laser beam 1710 when the first channel reaches the adjacent tissue 1718.

The treatment system 1700 can also include a delivery system (e.g., the delivery system described in FIG. 10) configured to deposit an active treatment agent in the at least first channel. In some implementations, the delivery system is configured to deposit the active treatment agent in the first channel by spraying the active treatment agent into the first channel. The active treatment agent can include one or more of a particulate, a liposome, a gel, a polymer, an emulsion, an ointment, a suspension, etc. The active treatment agent can include an anti-fungal drug approved for the treatment of onychomycosis. In some implementations, the delivery system can include a syringe (e.g., syringe illustrated in FIG. 10) that can include a disposable unit package and a sealant tip. The disposable unit package can store the active treatment agent. The sealant tip can be applied to the first channel after the deposition of the active treatment agent.

In some implementations, a cross-section of the first channel can be oriented perpendicular to the optical axis. The cross-section be one or more of circle, oval or rectangle. For example, if the laser beam 1710 is directed along the optical axis oriented along the z-axis, the cross-section can be oriented in the x-y plane, and can have one of the aforementioned shapes. In some implementations, the channel generation system 1702 can be configured to generate an array of channels in the target tissue 1716. As illustrated in FIG. 4B, the array of channels can be arranged in one or more of a square pattern, a triangular pattern, a quasi-random pattern, etc. The pitch of the array of channels can be based on a degree of infection in the target tissue 1716. For example, if the target tissue 1716 is highly infected, the pitch can be smaller. In some implementations, the array of channels can be generated by a plurality of laser sub-beams generated by splitting a laser beam (e.g., laser beam 1710) into the plurality of sub-beams.

In some implementations, a distance between the centers of adjacent channels in the array of channels can range between about 2 and 10 times, between about 3 and 7 times, between about 4 and 6 times, and between about 4 and 5 times the diameter of a channel in the array of channel (e.g., diameter in the cross-section of the channel perpendicular to the optical axis). In some implementations, a diameter of the channel at a proximal opening can range between about 30 microns to 200 microns. In some implementations, a spot diameter associated with the focal volume can be in the range of about 1 to about 25 micrometers.

Methods of treating various fungal infection (e.g., onychomycosis), such as for cosmetic purposes, can be carried out using the systems described herein. It is understood that although such methods can be conducted by a physician, the user can be a non-physician, such as an aesthetician, and other suitably trained personnel may use the systems described herein to treat onychomycosis with and without the supervision of a physician.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code) A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of non volatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. Accordingly, a value modified by a term or terms, such as "about" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

What is claimed is:

1. A treatment system, comprising:
a channel generation system comprising a laser configured to expose an infected region of a target tissue with a laser beam traveling along an optical axis and focused at a focal volume located in or adjacent to the target tissue, the laser beam having a wavelength ranging from about 100 nm to about 400 nm and configured to generate at least a first channel in the infected region;
a detection system comprising a sensor configured to detect a first radiation generated by one or more of (i) the target tissue, (ii) a fungi coupled to the infected region in the target tissue, and (iii) an adjacent tissue located proximal to the target tissue as a result of interaction with the laser beam; and
a delivery system comprising a reservoir configured to retain an active treatment agent and further configured to deposit the active treatment agent in the at least first channel;
wherein the channel generation system is configured to generate an array of channels in the target tissue, and wherein a pitch of the array of channels is based on a degree of infection in the target tissue.

2. The treatment system of claim 1, further comprising a controller configured to receive a first detection signal from the detection system indicative of the detected first radiation.

3. The treatment system of claim 2, wherein the first radiation is at least one of a fluorescence from the fungi and a fluorophore coupled to the fungi and wherein the controller is configured to determine the identity of the fungi based on the first detection signal.

4. The treatment system of claim 3, wherein the fluorophore includes one or more of 5-ALA, an ester of ALA, and ppIX.

5. The treatment system of claim 2, wherein the channel generation system is configured to generate at least a second channel adjacent to the first channel, the at least second channel configured to receive the active treatment agent, wherein the received active treatment agent in the first and second channels is configured to diffuse to portions of the target tissue adjacent to the first channel and the second channel.

6. The treatment system of claim 2, wherein the target tissue is a nail plate and the adjacent tissue is a nail bed tissue, and the first channel extends from a top proximal surface of the nail plate and a bottom distal surface of the nail plate, the bottom distal surface of the nail plate adjacent to a nail bed tissue.

7. The treatment system of claim 6, wherein the detection system is configured to detect a second radiation generated due to interaction between the laser beam and the nail bed tissue, and transmit a second detection signal indicative of interaction between the laser beam and the nail bed tissue, wherein the channel generation system is configured to terminate interaction between the laser beam and the nail plate based on reception of the second detection signal.

8. The treatment system of claim 1, further comprising a drilling system configured to generate one or more drilled holes in the target tissue.

9. The treatment system of claim 1, further comprising a driving system configured to drive the active treatment agent in the first channel by one or more of application of modulated pressure waves to the target tissue, application of heat to the target tissue, and application of an ultrasound wave to the target tissue.

10. The treatment system of claim 9, wherein the modulated pressure wave is generated by directing a second laser beam on the target tissue.

11. The treatment system of claim 1, wherein the delivery system is configured to deposit the active treatment agent in the first channel by at least spraying the active treatment agent into the first channel.

12. The treatment system of claim 1, wherein the delivery system includes a syringe comprising a disposable unit package comprising the active treatment agent and a sealant tip configured to be applied to the first channel after the deposition of the active treatment agent.

13. The treatment system of claim 1, wherein the active treatment agent includes one or more of a particulate, a liposome, a gel, a polymer, an emulsion, an ointment, and a suspension.

14. The treatment system of claim 1, wherein a cross-section of the first channel oriented perpendicular to the optical axis can be one of circle, oval or rectangle.

15. The treatment system of claim 1, wherein the array of channels in the target tissue is based on one or more of a rectangular pattern, a triangular pattern, a circular pattern, an oval pattern, a spiral pattern, and a quasi-random pattern.

16. The treatment system of claim 15, wherein the array of channels are generated by a plurality of laser sub-beams generated by splitting the laser beam into the plurality of sub-beams.

17. The treatment system of claim 15, wherein a distance between the centers of adjacent channels in the array of channels is one of between 2 and 10 times, between 3 and 7 times, between 4 and 6 times, and between 4 and 5 times the diameter of a channel in the array of channel.

18. The treatment system of claim 15, wherein a diameter of the channel at a proximal opening thereof is in the range of about 30 microns to 200 microns.

19. The treatment system of claim 1, wherein a spot diameter associated with the focal volume is about 1 to about 25 micrometers.

20. The treatment system of claim 1, wherein the active treatment agent includes one or more of an anti-fungal drug approved for the treatment of onychomycosis.

21. A method, comprising:
exposing, by a laser of a channel generation system, an infected region of a target tissue to a laser beam having a wavelength in the range of about 100 nm to about 400 nm and traveling along an optical axis, wherein the laser beam is focused at a focal volume located in or adjacent to the target tissue to form an array of channels in the target tissue, and wherein a pitch of the array of channels is based on a degree of infection in the target tissue;
detecting, by sensor of a detection system, a first radiation generated by one or more of the target tissue, a fungi coupled to the infected region in the target tissue, and an adjacent tissue located proximal to the target tissue as a result of interaction with the laser beam;
retaining, within a reservoir of a delivery system, an active treatment agent; and
depositing, by the delivery system, the active treatment agent in at least a first channel of the array of channels.

22. The method of claim 21, wherein the target tissue is a nail plate and the adjacent tissue is a nail bed tissue.

23. The method of claim 22, further comprising:
receiving, by a controller, a first detection signal from the detection system indicative of the detected first radiation, and
determining, by the controller, the identity of the fungi coupled to the infected region in the target tissue based on the first detection signal.

24. The method of claim 23, further comprising:

detecting, by the detection system, a second radiation generated due to interaction between the laser beam and the nail bed tissue, transmitting, by the detection system, a second detection signal indicative of interaction between the laser beam and the nail bed tissue, and terminating, by the channel generation system, the interaction between the laser beam and the nail plate based on reception of the second detection signal.

25. The method of claim 23, further comprising determining, via the controller, a depth associated with the first channel using at least one of reflectance confocal microscopy and optical coherence tomography.

26. The method of claim 21, further comprising, by a driving system, driving the active treatment agent in the first channels by one or more of applying modulated pressure waves to the target tissue, applying heat to the target tissue, and applying an ultrasound wave to the target tissue.

27. The method of claim 21, wherein the delivery system includes a syringe comprising a disposable unit package comprising the active treatment agent and a sealant tip, and further comprising applying the sealant tip to the first channels after the deposition of the active treatment agent.

28. The method of claim 21, further comprising softening the target tissue prior to exposure to the laser beam.

29. The method of claim 21, wherein the active treatment agent is at least one anti-fungal drug configured to treat onychomycosis.

30. The method of claim 21, wherein each channel of the array of channels extends from a top proximal surface of the target tissue to a bottom distal surface of the target tissue proximal to an adjacent tissue.

31. The method of claim 30, wherein each channel of the array of channels has an opening at the top proximal surface thereof with a dimension in the range of about 30 to 200 microns.

* * * * *